US012629444B2

(12) United States Patent
Denis et al.

(10) Patent No.: US 12,629,444 B2
(45) Date of Patent: May 19, 2026

(54) AIR TREATMENT UNIT

(71) Applicant: Carrier Corporation, Palm Beach Gardens, FL (US)

(72) Inventors: Prudence Denis, Culoz (FR); Olivier Josserand, Culoz (FR); Loris Rion, Culoz (FR); Franck Liaudet, Culoz (FR); Raphaël Di Paolo, Culoz (FR)

(73) Assignee: CARRIER CORPORATION, Palm Beach Gardens, FL (US)

( * ) Notice: Subject to any disclaimer, the term of this patent is extended or adjusted under 35 U.S.C. 154(b) by 790 days.

(21) Appl. No.: 17/951,335

(22) Filed: Sep. 23, 2022

(65) Prior Publication Data

US 2023/0100454 A1     Mar. 30, 2023

(30) Foreign Application Priority Data

Sep. 24, 2021     (EP) .................................... 21198920

(51) Int. Cl.
  *A61L 9/20*          (2006.01)
(52) U.S. Cl.
  CPC ............. *A61L 9/20* (2013.01); *A61L 2209/11* (2013.01); *A61L 2209/111* (2013.01); *A61L 2209/12* (2013.01); *A61L 2209/16* (2013.01)
(58) Field of Classification Search
  CPC .. A61L 9/20; A61L 2209/11; A61L 2209/111; A61L 2209/16; F24F 3/16; F24F 8/22
  See application file for complete search history.

(56) References Cited

U.S. PATENT DOCUMENTS

| | | | | |
|---|---|---|---|---|
| 5,523,057 | A | * | 6/1996 | Mazzilli .................... A61L 9/20 |
| | | | | 250/436 |
| 6,099,406 | A | | 8/2000 | Demster |
| 6,716,406 | B2 | * | 4/2004 | Reisfeld ................... F24F 8/22 |
| | | | | 95/12 |
| 7,740,686 | B2 | | 6/2010 | Metteer |
| 8,772,744 | B1 | | 7/2014 | Liu |
| 2018/0147312 | A1 | | 5/2018 | Ryerson |

FOREIGN PATENT DOCUMENTS

WO        2016116656 A1      7/2016

OTHER PUBLICATIONS

Author Unknown, "Lighting Answers: UV Disinfection Products", vol. 14, Issue 1, Dec. 31, 2020, pp. 1-55, XP055841589, Retrieved from the Internet: URL:https://www.Ire.rpi.edu/programs/NLPIP /lightingAnswers/pdf/view/LA_UVDisinfection.pdf.
European Search Report for Application No. 21198920.7; Issued Mar. 18, 2022; 9 Pages.

* cited by examiner

*Primary Examiner* — Lessanework Seifu
(74) *Attorney, Agent, or Firm* — CANTOR COLBURN LLP

(57)                ABSTRACT
An air treatment unit 10 for attachment to a fan coil unit 12 for treating air from an indoor setting, the air treatment unit 10 including: an inlet 14 for connection to a ducting system that receives indoor air; a treatment volume 22 for receiving air flow from the inlet 14; a UV-C light source 24 within the treatment volume 22 for exposing the air in the treatment volume 22 to UV-C radiation; and an outlet 16 for discharge of treated air to the fan coil unit 12, the outlet 16 is configured for connection to an inlet plenum 18 of the fan coil unit 12.

19 Claims, 3 Drawing Sheets

AIR TREATMENT UNIT

FOREIGN PRIORITY

This application claims priority to European Patent Application No. 21198920.7, filed Sep. 24, 2021, and all the benefits accruing therefrom under 35 U.S.C. § 119, the contents of which in its entirety are herein incorporated by reference.

TECHNICAL FIELD OF INVENTION

The present invention relates to an air treatment unit for treatment of air from an indoor setting, where the air treatment unit is for fitting to a fan coil unit. It also relates to a corresponding method of treating air.

BACKGROUND OF THE INVENTION

It is important for the health and safety of occupants within in an indoor setting that the indoor air quality is above a certain threshold. In recent times there has been a particular focus on protecting occupants from biological agents such as viruses. The presence of viral particles, especially in high concentrations, can lead to the spread of contagious diseases throughout the occupants of the room. It is possible to treat air to restrict spread of viruses by filtering the indoor air using high filter efficiency filters, but this greatly increases the power needed due to the high pressure drop across filters with high filter efficiencies. It would therefore be beneficial to provide an air treatment system that can increase the indoor air quality by treatments at biological agents such as viruses but to avoid the need for a high filter efficiency filter.

SUMMARY OF THE INVENTION

According to a first aspect of the invention, there is provided an air treatment unit for attachment to a fan coil unit for treating air from an indoor setting, wherein the air treatment unit comprises: an inlet for connection to a ducting system that receives indoor air; a treatment volume for receiving air flow from the inlet; a UV-C light source within the treatment volume for exposing the air in the treatment volume to UV-C radiation; and an outlet for discharge of treated air to the fan coil unit, wherein the outlet is configured for connection to an inlet plenum of the fan coil unit.

With the above treatment unit it is possible to easily modify a system with a pre-existing fan coil unit to add an added air treatment capability where UV-C radiation can be used to deactivate the DNA of biological agents, in particular viruses. Thus, upon new installation or as a retrofit for previously installed fan coil units it becomes possible to add in the proposed treatment unit to thereby introduce UV-C sterilisation of the air along with other functions of the fan coil unit, e.g. with a HVAC system. In some implementations the treatment unit is advantageously configured, with knowledge of the fan coil unit operation, in order to provide a minimum dosage level of 25 J/m2 of UV-C for the air. This has been shown to deactivate the majority of SARs-CoV-2 virus, typically over 90%, as well as also deactivating the DNA of other viruses such as Influenza. UV-C treatments have been previously proposed within HVAC systems, but typically for deactivating biological contaminants on surfaces, or with differing implementations not involving a module for connection to the fan coil unit inlet plenum.

A dosage of 25 J/m2 may be provided by selecting a UV-C light source of suitable intensity for the intended air flow rate of the fan coil unit, i.e. the expected air flow rate through the treatment volume. For example, the UV-C light source may be selected for a minimum dose of 25 J/m2 at an air flow rate in the range 200-400 m3/h, optionally 250-350 m3/h such as an air flow rate of about 300 m3/h.

The UV-C light source comprises one or more UV-C lamps producing UV radiation at one or more wavelengths in the UV-C range, i.e. 100-280 nm wavelength. The UV-C light source may produce radiation with wavelength in the range 240-280 nm or 250-260 nm, such as light at a wavelength of about 254 nm. Such wavelengths are found to be effective at deactivating viral DNA.

The UV-C light source may provide radiation with an intensity of 900 to 1200 lumens. A mercury vapour lamp with 19 W UVC output may be used.

In example embodiments the air treatment unit comprises a housing with openings for the inlet and the outlet, wherein the treatment volume is contained within the housing.

The inlet of the air treatment unit is configured to connect to the ducting system and may advantageously have similar design to the fan coil unit inlet plenum in order to connect to pre-existing connectors of the ducting system. The outlet is configured for connection to the inlet plenum of the fan coil unit. In one example the connection may involve detaching an inlet part of the fan coil unit to expose an inner plenum of the inlet plenum, with the air treatment unit having an outlet opening configured to connect to this inner plenum. Alternatively/additionally, the inlet and the outlet may therefore provide a connection pair, with the outlet of the air treatment unit being of a design that would be connectable to the inlet of the air treatment unit. In this way the air treatment unit may be fitted to an existing fan coil unit via the existing ducting system components (provided for connection to the fan coil unit inlet plenum) without the need for any added parts for ensuring connection compatibility.

The housing may comprise a maintenance door for providing access within the treatment volume, such as for inspection and maintenance of the UV-C light source, e.g. for replacement of a UV-C lamp of the UV-C light source. The maintenance door may be provided with a safety cut off configured to disable the UV-C light source when the maintenance door is used. The safety cut off may hence ensure safety of the user, as well as protecting the surrounding environment, by preventing UV-C radiation from being emitted when the maintenance door is open. The safety cut off may be configured to disable the UV-C light source by disconnecting the UV-C light source from its power supply or by otherwise deactivating the UV-C light source. The safety cut off may for example be a switch device, such as a mechanical switch, a relay, an electromechanical switch or some other device capable of triggering disabling of the UV-C light source in response to the use of the maintenance door. The use of the maintenance door may comprise opening of the door or of a latch of the door. Alternatively or additionally it may comprise unlocking of a lock of the door. The safety cut off may be arranged to re-enable the UV-C light source when the door is no longer in use, such as when the door is re-closed, latched or locked as the case may be. The safety cut off may optionally be configured to wait for a set time period after the door is no longer in use before the UV-C light source is re-enabled.

The housing may provide structural support for the UV-C light source. It may be configured to be held from outside by its connection at the outlet to the fan coil unit plenum and by its connection at the inlet to the ducting system. Alternatively or additionally it may be configured to mount to brackets to a building, such as brackets provided for holding the fan coil unit and/or part(s) of the ducting system. The air treatment unit may be arranged for installation in a false ceiling along with the fan coil unit.

To prevent the UV-C radiation from escaping the housing the treatment unit may comprise UV-C shielding around the treatment volume. The UV-C shielding may be configured to prevent at least 80% or at least 90% of the UV-C light from leaving the housing. The UV-C shielding may have solid unbroken surfaces where there is no need for air flow. Where the housing has solid sides then the house material may provide the required UV-C shielding. In the air flow path the UV-C shielding may comprise openings for the air flow, for example it comprise perforated plates and/or an air path with one or more direction changes in order to permit air flow but block line of sight for the UV-C radiation.

The housing may include an inspection opening for allowing a person to see, from the outside, if the UV-C light source is active. The inspection opening may be configured to allow transmission of visible light but to block UV-C light.

Electrical power for the UV-C light source may be provided via connection to the same power supply as the fan coil unit. Thus, the air treatment unit may be configured for connection to the fan coil unit power supply, such as to a pre-existing connection on the fan coil unit.

The air treatment unit may be configured to detect occupancy of the indoor space and to deactivate the UV-C light source when the indoor space is unoccupied and/or to only permit it to activate when the indoor space is occupied. For example, the air treatment unit may comprise a $CO_2$ sensor for determining when the indoor space is occupied. The air treatment unit may be configured to activate the UV-C light source in response to operation of the fan coil unit, such as in response to operation of the fan thereof. For example the UV-C light source may be activated at a set time period after the fan is activated, for example 5 minutes. Incorporating a time period of this type avoids on-off cycling of the UV-C lamp when the fan coil unit is only operating intermittently.

The air treatment unit may be arranged to detect operation of the fan coil unit, for example via an air flow sensor, or alternatively it may be configured to interact with a control system of the fan coil unit, for example being connected to the fan coil unit to enable it to receive a signal indicating that the fan coil unit is operating, i.e. that the fan of the fan coil unit is running. The fan coil unit may be modified in order to provide it with a controller having a dedicated output for control of the UV-C light source. When the air treatment unit is configured to interact with a control system of the fan coil unit then this may also allow for the air treatment unit to receive input from the control system regarding occupancy of the indoor space and/or other control inputs, such as indications of variations in air flow rate, where the fan coil unit can vary the flow rate, so that the UV-C light source can be controlled accordingly to maintain a required dosage level.

The invention extends to a system comprising the air treatment unit and the fan coil unit, wherein the outlet of the air treatment unit is coupled to the inlet plenum of the fan coil unit. The fan coil unit comprises a fan for generating air flow and a coil for heat exchange with the air flow. It may also include other features, such as sensors and/or filters. This system may include a common power supply for powering both of the fan coil unit and the air treatment unit. The combination of the air treatment unit and the fan coil unit may also include interconnection of control systems or a common control system, wherein operation of the air treatment unit can coordinated with operation of the fan coil unit, such as with the features discussed above in connection with occupancy control and/or operation of the UV-C light tied to operation of the fan of the fan coil unit. Optionally, where the air treatment unit includes a maintenance door and associated safety cut off then the system may be arranged to deactivate the fan of the fan coil unit when the maintenance door is in use.

The air treatment unit may be arranged to operate in conjunction with the fan coil unit to produce a minimum UV-C dosage rate of 25 J/m2 as discussed above. Thus, the intensity of the UV-C light source may be selected to provide such a dosage when the air flow through the air treatment unit is at the design air flow rate for the fan coil unit. This air flow rate may be in one of the ranges discussed above, for example it may be about 300 m3/h. The fan coil unit and the air treatment unit may be configured to enable varying of the UV-C dosage rate via varying the intensity of the UV-C light and/or by varying the air flow rate, such as via variable fan coil unit fan speed and/or controllable dampers of the fan coil unit. Increasing intensity of UV-C radiation or decreasing the air flow rate will increase the dosage, and vice versa. In one example, the dosage rate may be variable up to 100 J/m2, thereby acting to deactivate DNA of a greater range of viruses and other biological agents.

Viewed from a second aspect, the invention extends to a method of installation of the air treatment unit, comprising providing an air treatment unit with any of the features as described above and fitting the outlet of the air treatment unit to the inlet plenum of a fan coil unit. The inlet of the air treatment unit may be fitted to a ducting system provided for the fan coil unit. This method may be done to retrofit the air treatment unit to a pre-existing fan coil unit, or it may be done as a part of an installation of a bigger system, i.e. concurrent with installation of the fan coil unit and/or the ducting system. The method of installation of the air treatment unit may include calibration of the air treatment unit to set the intensity of the UV-C light source based on the intended air flow rate of the fan coil unit. This calibration may be done in order to achieve a required dosage level of the UV-C, such as the minimum 25 J/m2 dose discussed above.

According to a further aspect of the invention, there is provided a method of treating air from an indoor setting comprising using the air treatment unit of the first aspect and/or with any other feature discussed above. The method may comprise operating the UV-C light source in reaction to operation of the fan of the fan coil unit, e.g. including a delay as discussed above. The method may comprise occupancy based operation of the UV-C light source as discussed above. The treating of air may be for deactivating viral DNA, and the air treatment unit may be used for providing a minimum dosage of 25 J/m2 of UV-C radiation to the air that passes through it to the fan coil unit.

BRIEF DESCRIPTION OF THE DRAWINGS

The present invention will now be described, by way of example only, with reference to the accompanying drawings, in which.

DETAILED DESCRIPTION OF THE INVENTION

Figure 1:
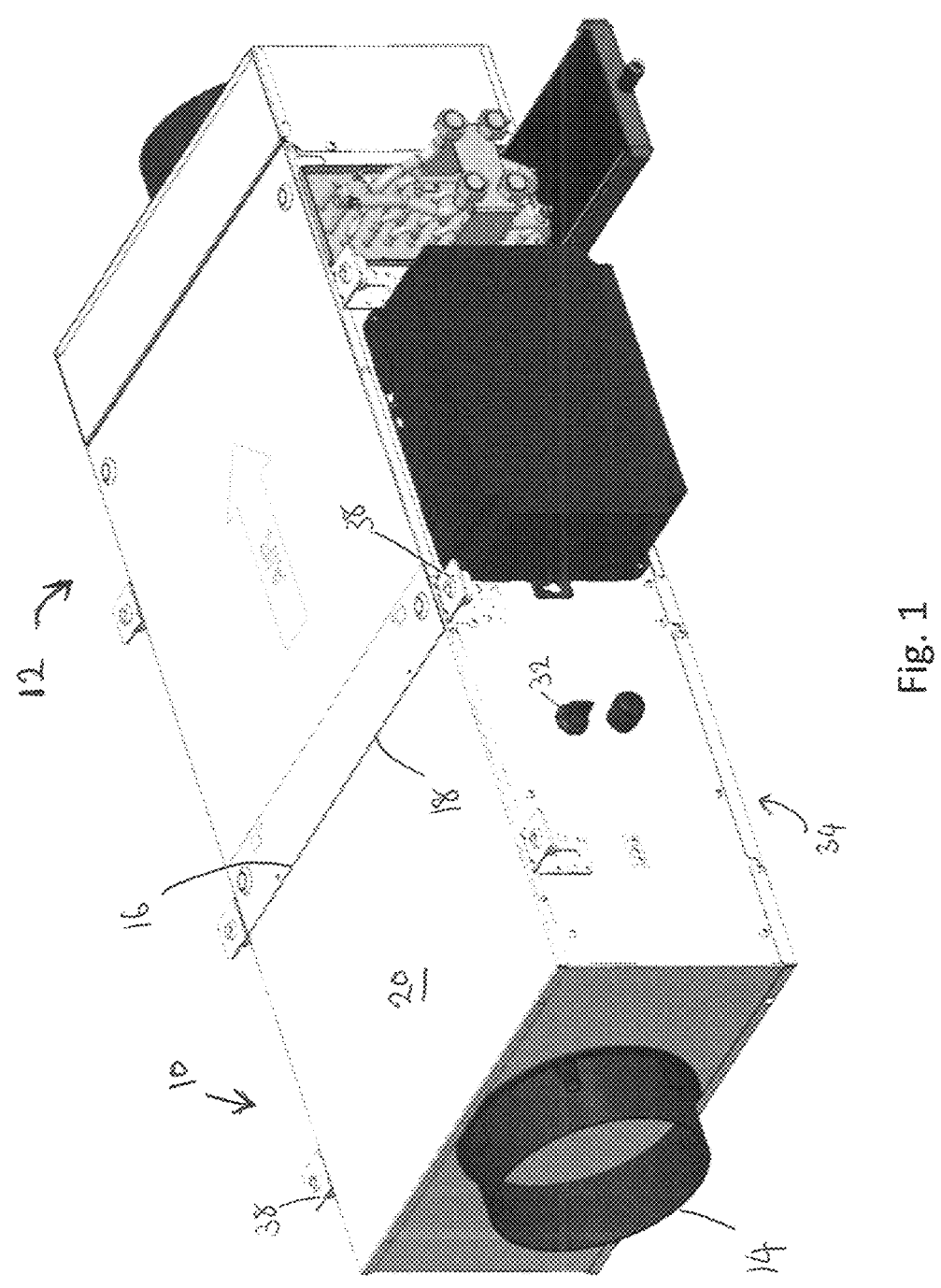
FIG. 1 shows an air treatment unit connected to a fan coil unit.

FIG. 1 shows an air treatment unit 10 connected to a fan coil unit 12. This can be done as a modification to a system with a pre-existing fan coil unit 12 to add an added air treatment capability, or it can be done along with installation of the fan coil unit 12. The air treatment unit 10 is for providing UV-C radiation treatment of the air in order to deactivate the DNA of viruses, as well as giving other sterilisation effects. In this example the treatment unit is advantageously configured in order to provide a minimum dosage level of 25 J/m2 of UV-C for the air based on the expected air flow rate of the fan coil unit 12.

Figures 2, 3:
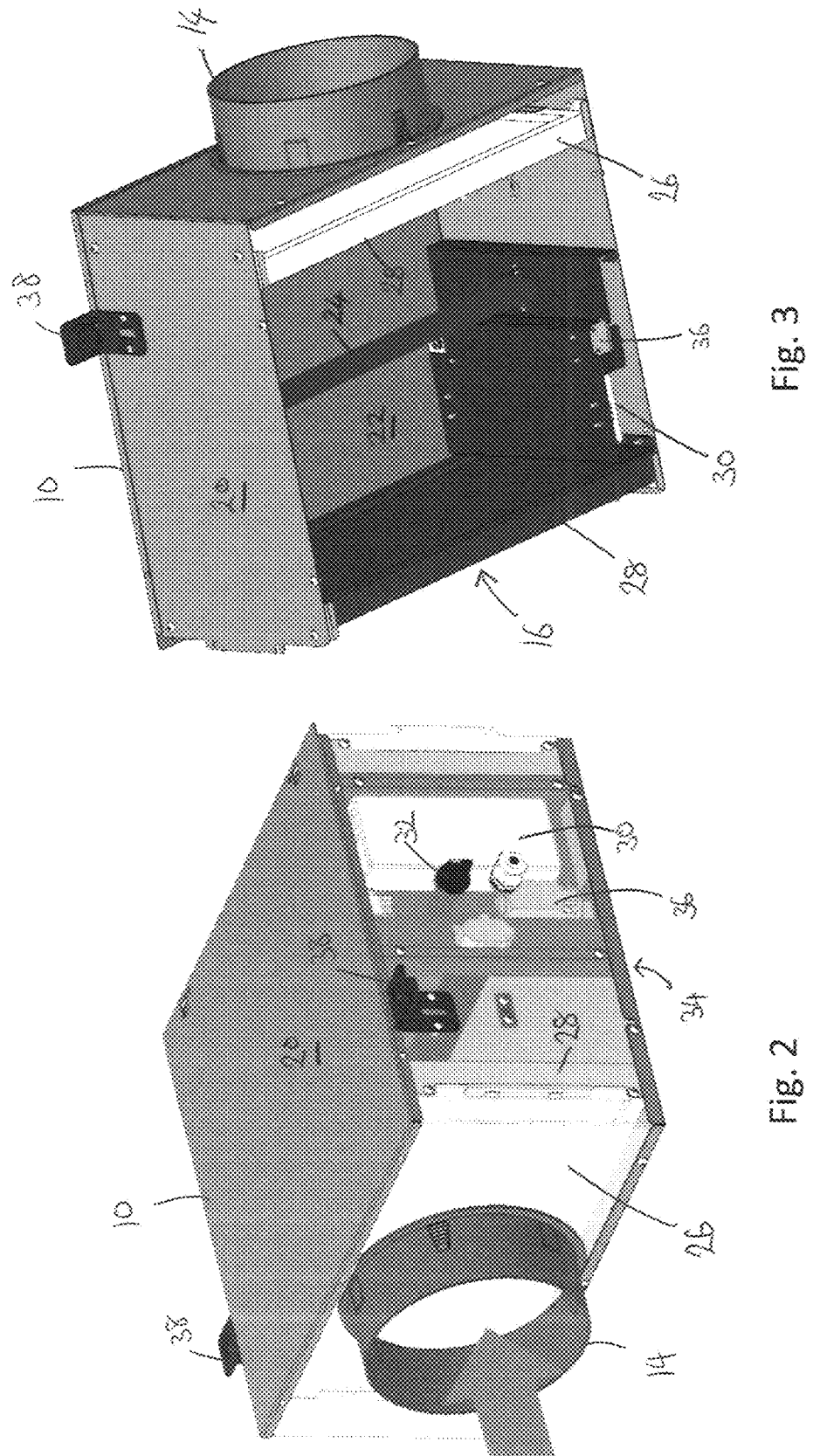
FIG. 2 shows the air treatment unit of FIG. 1 without the fan coil unit and with housing parts removed to show internal detail.
FIG. 3 is another view of the air treatment unit of FIG. 1 with a lower maintenance door removed.

The air treatment unit includes an inlet 14 for connection to a ducting system, and an outlet 16 for connection to the inlet plenum 18 of the fan coil unit 12. FIGS. 2 and 3 show further detail of the inlet 14 and outlet 16 as well as added details of the air treatment features of the air treatment unit 10. In particular, an outer housing 20 of the air treatment unit 10 encloses a treatment volume 22, within which a UV-C light source 24 is provided for exposing air in the treatment volume to UV-C radiation at the required dosage. The UV-C light source 24 includes at least one UV-C lamp, e.g. an LED lamp or fluorescent tube, may produce radiation with wavelength in the range 240-280 nm or 250-260 nm, such as light at a wavelength of about 254 nm. In this example the UV-C light source 24 is a mercury vapour lamp that provides radiation with 19 W UVC output.

As seen in FIGS. 2 and 3 the air treatment unit 10 includes a filter 26 adjacent the inlet 14 for removing particles from the air flowing into the unit 10. UV shielding 28 is provided at the outlet 16, to prevent UV exposure of the fan coil unit 12, and at the filter 26 to protect the filter 26 and prevent UV from being emitted into the ducting. The walls of the housing 20 also act as UV shielding elements. Thus, the UV-C radiation from the UV-C light source 24 is contained within the treatment volume 22. The air treatment unit 10 also includes control and power circuitry 30, which can include a controller for activating the UV-C light source 24 and/or ballast for the UV-C light source 24. A switch 32 is included for activating and deactivating the UV-C light source 24, which may be done under control of the controller.

The housing 20 further comprises a maintenance door 34, in this case at the bottom in the orientation shown in FIGS. 2 and 3. The maintenance door 34 is for providing access within the treatment volume 22, such as for inspection and maintenance of the UV-C light source 24, e.g. for replacement of a UV-C lamp of the UV-C light source 24. The maintenance door 34 is provided with a safety cut off configured to disable the UV-C light source 24 when the maintenance door 34 is used. In this example the safety cut off includes a door contact 36 connected to the switch 32, whereby opening of the door 34 will disable the UV-C light source 24 by action of the door contact 36 and switch 32 to disconnect the UV-C light source from its power supply.

The housing 20 may provide structural support for the various parts discussed above including the UV-C light source 24. It is supported in place by its connection at the outlet 16 to the fan coil unit plenum 18 and by its connection at the inlet 14 to the ducting system, as well as being supported by brackets 38 for mounting to a building or structures within the building. The air treatment unit 10 in this example is arranged for installation in a false ceiling of a room in a building along with the fan coil unit 12, where they form a part of the buildings HVAC system.

The air treatment unit 10 and/or the fan coil unit 12 detect occupancy of the indoor space. This allows the air treatment unit 10 to deactivate the UV-C light source 24 when the indoor space is unoccupied and/or to only permit it to activate when the indoor space is occupied. By way of example, the air treatment unit 10 or the fan coil unit 12 can comprise a CO2 sensor for determining when the indoor space is occupied. In addition, the air treatment unit 10 may be configured to activate or deactivate the UV-C light source 24 in response to the operation status of the fan coil unit 12, in particular based on operation of a fan thereof.

Advantageously, the air treatment unit 10 is configured to interact with a control system of the fan coil unit 12, for example being connected to the fan coil unit 12 to enable it to receive a signal indicating that the fan coil unit 12 is operating, i.e. that the fan of the fan coil unit is running. This optionally also allows for the air treatment unit 10 to receive input from the fan coil unit control system regarding occupancy of the indoor space and/or other control inputs, such as indications of variations in air flow rate. In cases where the fan coil unit 12 can vary the air flow rate then the intensity of the UV-C light source 24 can advantageously be controlled in order to maintain a required dosage level.

It will be understood that installation of the air treatment unit 10 is simple since it is designed to fit directly to the fan coil unit 12. Installation hence comprises fitting the outlet 16 of the air treatment unit 10 to the inlet plenum 18 of the fan coil unit 12, which may already have been installed in the building. The air treatment unit 10 can be retrofitted to a pre-existing fan coil unit 12, or it may be done as a part of an installation of a bigger system, i.e. concurrent with installation of the fan coil unit 12 and/or the ducting system. The installation of the air treatment unit 10 may include calibration to set the intensity of the UV-C light source 24 based on the intended air flow rate of the fan coil unit 10, in particular in order to achieve a required dosage level of the UV-C, such as the minimum 25 J/m2 dose discussed above.

Figure 4:
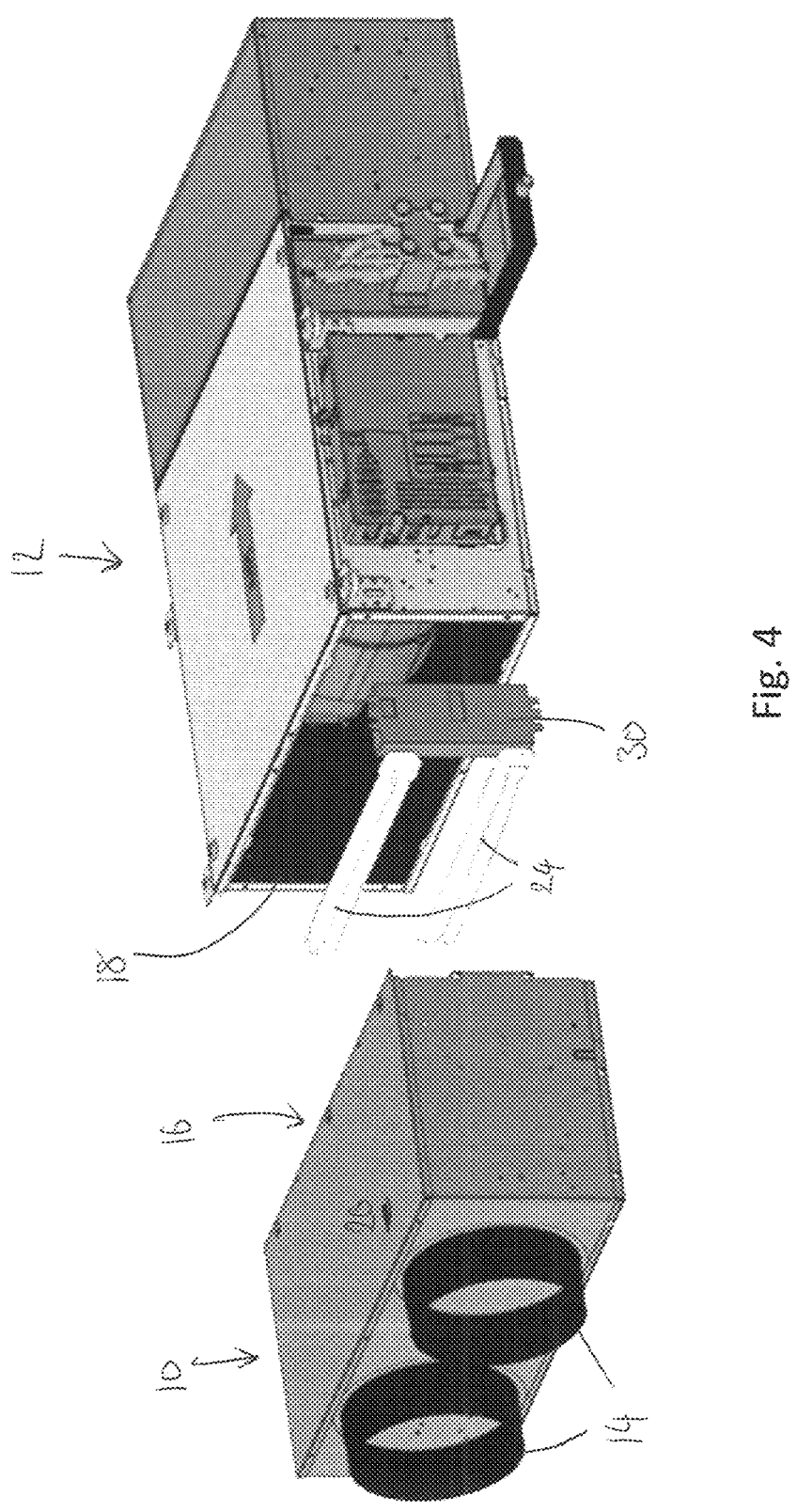
FIG. 4 shows another example of an air treatment unit with a different inlet configuration.

FIG. 4 shows another example of an air treatment unit 10, in this case for connection to a double ducting arrangement. This example therefore has a differing configuration for the inlet 14, but it may be otherwise similar to the air treatment unit 10 of FIGS. 1 to 3.

What is claimed is:

1. A retrofittable air treatment unit for attachment to a fan coil unit for treating air from an indoor space, wherein the retrofittable air treatment unit comprises:

an inlet for connection to a ducting system that receives air from the indoor space;

a treatment volume for receiving air flow from the inlet;

a UV-C light source within the treatment volume for exposing the air in the treatment volume to UV-C radiation;

an outlet for discharge of treated air to the fan coil unit, wherein the outlet is configured for connection to an inlet plenum of the fan coil unit; and a $CO_2$ sensor for determining if the indoor space is occupied.

2. The retrofittable air treatment unit as claimed in claim 1, wherein the retrofittable treatment unit comprises a UV-C light source of suitable intensity for the intended air flow rate of the fan coil unit to provide a minimum dosage level of 25 $J/m^2$ of UV-C for the air in the treatment volume.

3. The retrofittable air treatment unit as claimed in claim 1, wherein the UV-C light source is configured to provide a minimum dose of 25 J/m² at an air flow rate in the range 200-400 m³/h.

4. The retrofittable air treatment unit as claimed in claim 1, wherein the retrofittable air treatment unit comprises a housing with openings for the inlet and the outlet, wherein the treatment volume is contained within the housing.

5. The retrofittable air treatment unit as claimed in claim 4, wherein the housing comprises a maintenance door for providing access within the treatment volume; and wherein the maintenance door is provided with a safety cut off configured to disable the UV-C light source when the maintenance door is used.

6. The retrofittable air treatment unit as claimed in claim 5, wherein the use of the maintenance door comprises opening of the door or of a latch of the door, and/or wherein use of the maintenance door comprises unlocking of a lock of the door.

7. The retrofittable n air treatment unit as claimed in claim 5, wherein the safety cut off is arranged to re-enable the UV-C light source when the maintenance door is no longer in use.

8. The retrofittable air treatment unit as claimed in claim 4, wherein the retrofittable treatment unit comprises UV-C shielding around the treatment volume for preventing the UV-C radiation from escaping the housing, and wherein in the air flow path the UV-C shielding comprises openings in order to permit air flow but block line of sight for the UV-C radiation.

9. The retrofittable air treatment unit as claimed in claim 4, wherein the housing includes an inspection opening for allowing a person to see, from the outside, if the UV-C light source is active; and wherein the inspection opening is configured to allow transmission of visible light but to block UV-C light.

10. The retrofittable air treatment unit as claimed in claim 1, wherein the retrofittable air treatment unit is configured to detect occupancy of the indoor space in order to deactivate the UV-C light source when the indoor space is unoccupied and/or to only permit it to activate when the indoor space is occupied.

11. The retrofittable air treatment unit as claimed in claim 1, wherein the retrofittable air treatment unit is configured to activate the UV-C light source in response to operation of the fan coil unit.

12. The retrofittable air treatment unit as claimed in claim 11, wherein the retrofittable air treatment unit is configured to interact with a control system of the fan coil unit to enable it to receive a signal indicating that the fan coil unit is operating.

13. The retrofittable air treatment unit as claimed in claim 11, wherein the UV-C light source is activated at a set time period after the fan of the fan coil unit is activated.

14. A system comprising the retrofittable air treatment unit of claim 1 and a fan coil unit, wherein the outlet of the retrofittable air treatment unit is coupled to the inlet plenum of the fan coil unit.

15. A system as claimed in claim 14, wherein the fan coil unit has a controller having a dedicated output for control of the UV-C light source.

16. The retrofittable air treatment unit as claimed in claim 14, wherein the fan coil unit provides input to the air treatment unit regarding occupancy of the indoor space.

17. A method of installation of the retrofittable air treatment unit as claimed in claim 1, the method comprising:
  providing the retrofittable air treatment unit; and
  fitting the outlet of the air retrofittable treatment unit to the inlet plenum of a fan coil unit.

18. A method of treating air from an indoor space comprising: using the retrofittable treatment unit of claim 1 and operating the UV-C light source to expose the air to UV-C radiation.

19. The method of treating air from an indoor space as claimed in claim 18, wherein operating the UV-C light source to expose the air to UV-C radiation is in response to the $CO_2$ sensor determining that the indoor space is occupied.

* * * * *